United States Patent
Musa

(10) Patent No.: US 6,620,905 B1
(45) Date of Patent: Sep. 16, 2003

(54) CURABLE COMPOSITIONS CONTAINING BENZOXAZINE

(75) Inventor: Osama M. Musa, Hillsborough, NJ (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 0 days.

(21) Appl. No.: 10/080,738

(22) Filed: Feb. 23, 2002

(51) Int. Cl.7 .............................................. C08G 73/06
(52) U.S. Cl. ........................ 528/423; 528/422; 525/203; 525/205; 525/206; 525/330.9
(58) Field of Search ................................ 528/423, 422; 525/203, 205, 206, 330.9

(56) References Cited

U.S. PATENT DOCUMENTS

| | | |
|---|---|---|
| 5,543,516 A | 8/1996 | Ishida |
| 5,900,447 A | 5/1999 | Ishida |
| 5,973,144 A | 10/1999 | Ishida |
| 6,207,786 B1 | 3/2001 | Ishida et al. |
| 6,437,026 B1 | 8/2002 | Garrett |
| 2002/0128354 A1 | 9/2002 | Garrett |

FOREIGN PATENT DOCUMENTS

WO    WO 01/34581 A1    5/2001

OTHER PUBLICATIONS

Takeichi et al; Synthesis and preperties of polybenzoxazine based composites; 2000, Transworld research network, Chem Abstract 136: 263860.*

Agag et al; Effect of hydroxyphenylmaleimide on the curing behvaiour and thermomechnical of rubber modified polybenzoazine; 2001; Institute of physics publishing; Chem Abstract 135: 227365.*

Kim et al; Synthesis and thermal characterization of polybenxozazines based on acetylene functional monomers; 1998; Society for the advancement of material and process engineering; Chem Abstract 129: 331125.*

S. Rimdusit, H. Ishida; Development of new class of electronic packaging materials based on ternary systems of benzoxazine, epoxy, and phenolic resins; *Polymer* 41 (2000) 7941–7949; Elsevier Pub.

* cited by examiner

*Primary Examiner*—Duc Truong
(74) *Attorney, Agent, or Firm*—Jane E. Gennaro

(57) ABSTRACT

Curable compositions comprise a benzoxazine compound or resin in combination with at least one additional curable compound or resin. Optionally, the composition will further comprise a curing agent and/or a filler. These compositions have utility as adhesives, coatings and encapsulants, especially for use within the semiconductor fabrication industry, with particular utility as die attach adhesives, films, and underfill materials, such as no-flow underfills, capillary flow underfills, wafer level underfills, and as lead free solders.

10 Claims, No Drawings

CURABLE COMPOSITIONS CONTAINING BENZOXAZINE

FIELD OF THE INVENTION

This invention relates to curable compositions containing compounds or resins having a benzoxazine moiety.

BACKGROUND OF THE INVENTION

Curable compositions are used in the fabrication and assembly of semiconductor packages and microelectronic devices, such as in the bonding of integrated circuit chips to lead frames or other substrates, in the bonding of circuit packages or assemblies to printed wire boards, or in encapsulants, underfills, or coating materials. There are a number of curable compositions that are used in the industry, but not all these give as full a performance as is needed for all uses.

Monobenzoxazine and polybenzoxazine compounds and resins (hereinafter benzoxazines) add to the spectrum of performance materials for use within the semiconductor fabrication industry. These compounds are formed by the reaction of a mono-phenol, a mono- or poly-amine (primary) and formaldehyde or of a mono-amine (primary), a polyphenol, and formaldehyde. They exhibit good heat resistance, electronic properties, low water absorption, no out-gassing, low dielectric constant, and almost no shrinkage on cure. However, on their own, they have limited processability because of their high viscosity, and they tend to be brittle and require more flexibility for use in electronic devises.

SUMMARY OF THE INVENTION

This invention is a curable composition containing at least one monobenzoxazine or polybenzoxazine moiety (benzoxazine) and at least one other curable resin or compound. For purposes of this specification, a benzoxazine compound is one that contains at least one of the structure:

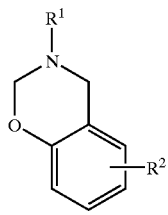

in which $R^1$ and $R^2$ are any organic moiety, including another benzoxazine structure. The composition optionally may comprise a curing agent and/or a filler. The composition can be in the form of a paste, prepared by blending or milling, or a film, prepared by standard film making techniques known to those skilled in the art. These compositions have utility as adhesives, coatings and encapsulants, especially for use within the semiconductor fabrication industry. They have particular utility as die attach adhesives and films, and underfill materials, such as no-flow underfills, capillary flow underfills, wafer level underfills, and as lead free solders.

DETAILED DESCRIPTION OF THE INVENTION

The benzoxazine compound will contain at least one of the structure disclosed above, and, in general, any benzoxazine or polybenzoxazine containing compound can be used in the curable composition. Benzoxazine compounds are described, for example, in U.S. Pat. No. 5,543,516 and WO 99/18092. Suitable benzoxazine compounds include those of the formula

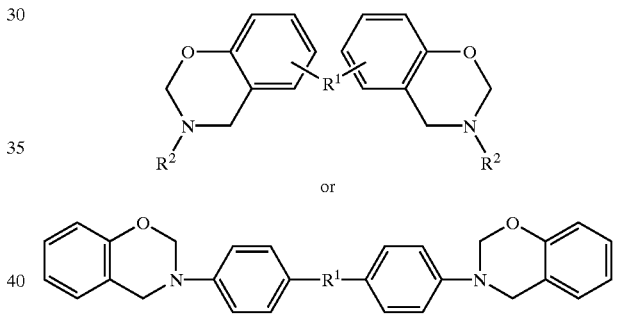

in which $R^1$ is a divalent radical that may be aliphatic, aromatic, or a combination of aliphatic and aromatic, and that may contain heteroatoms, such as oxygen, nitrogen, sulfur, phosphorous, or halogen, or that may be a single bond, or that may be S, $S_2$, SO, $SO_2$, O, or CO; and $R^2$ is hydrogen, an alkyl or substituted alkyl, an aromatic or substituted aromatic. Suitable and preferred benzoxazine compounds are:

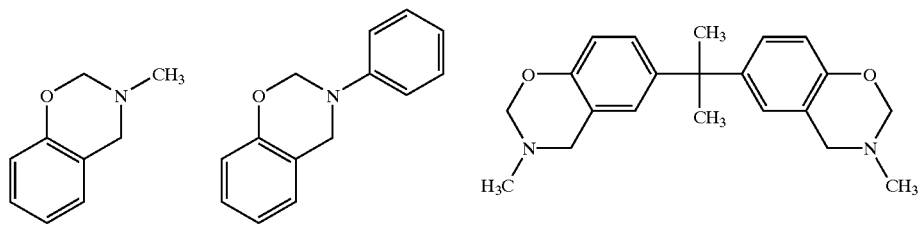

-continued
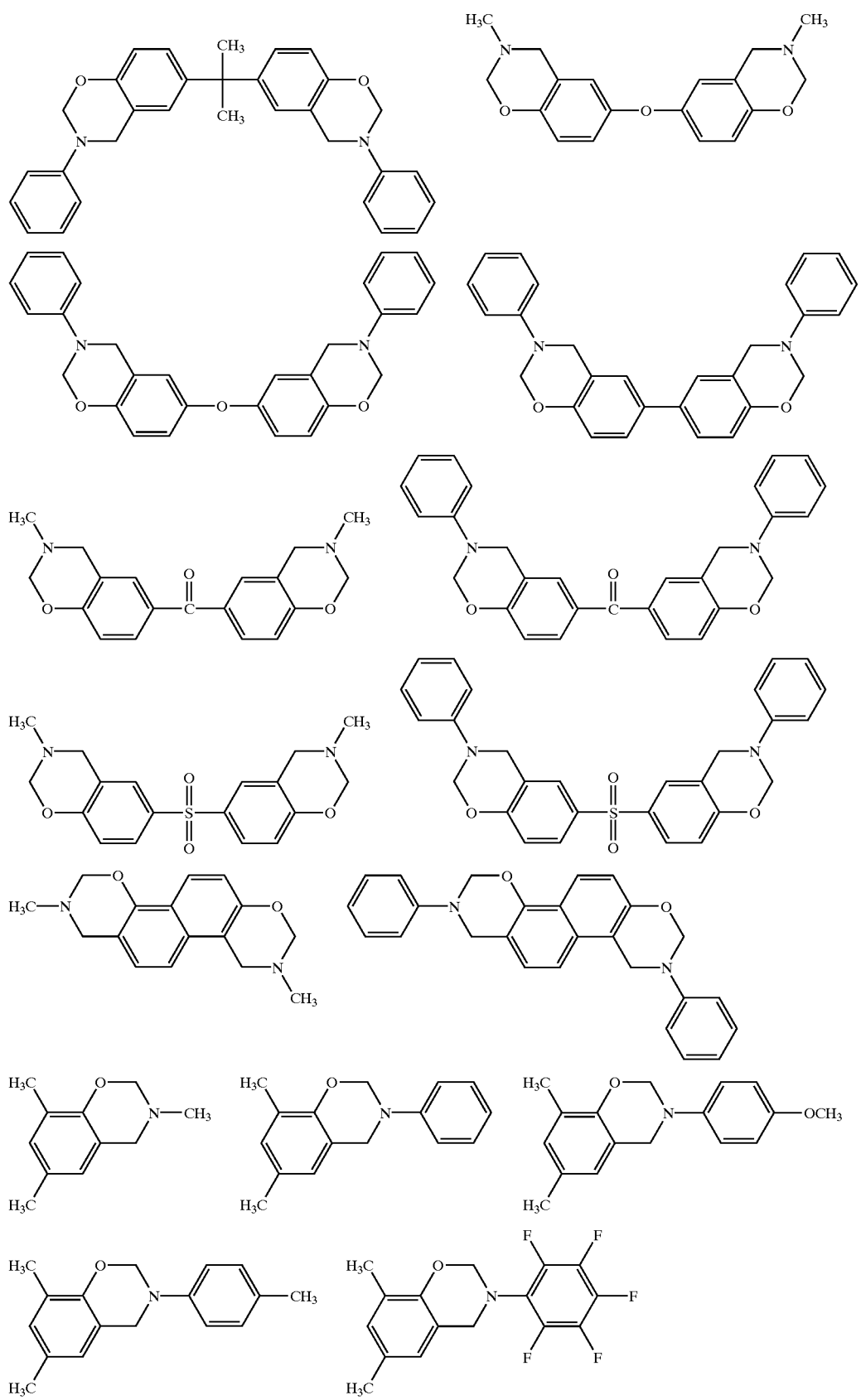

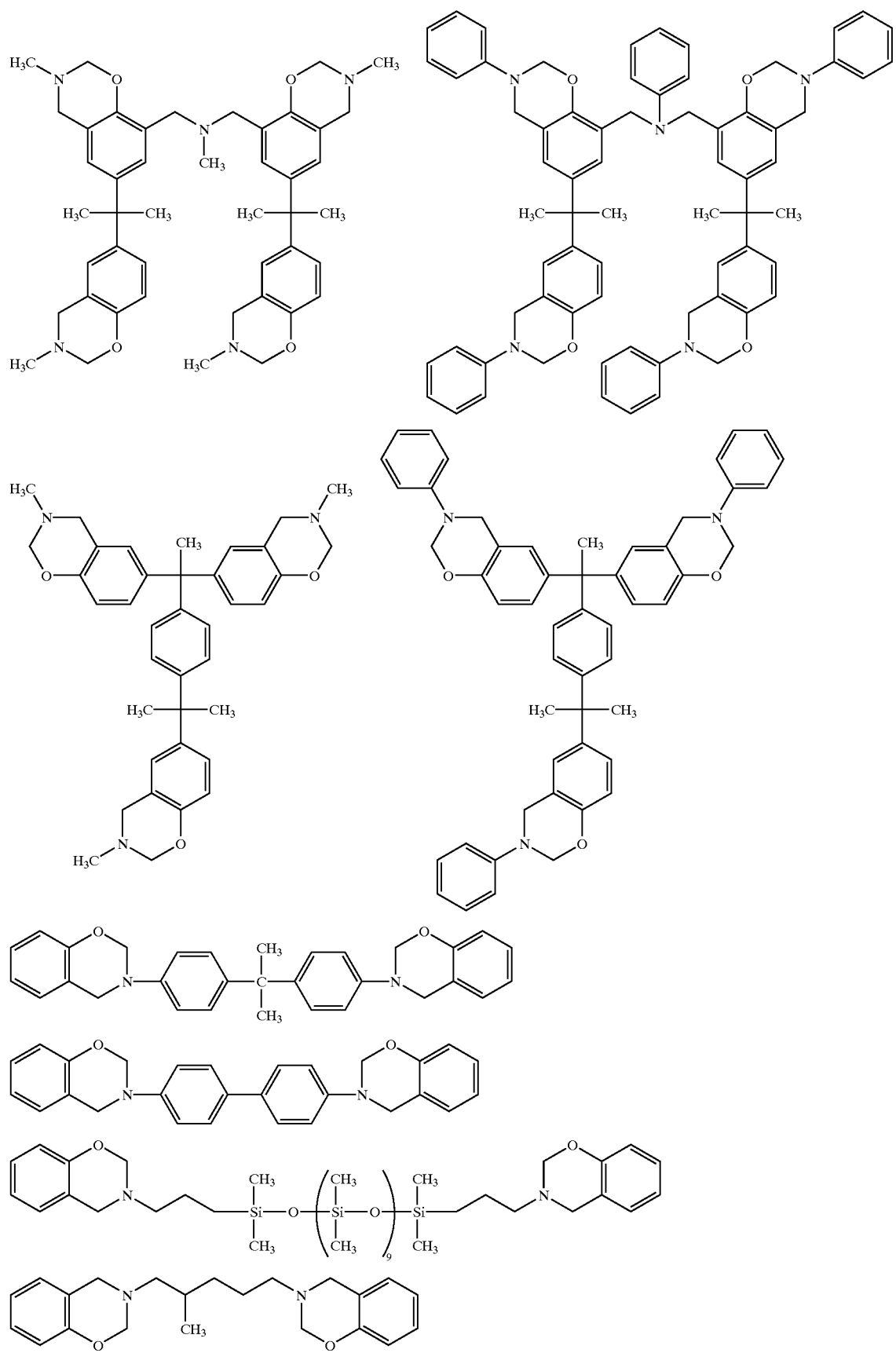

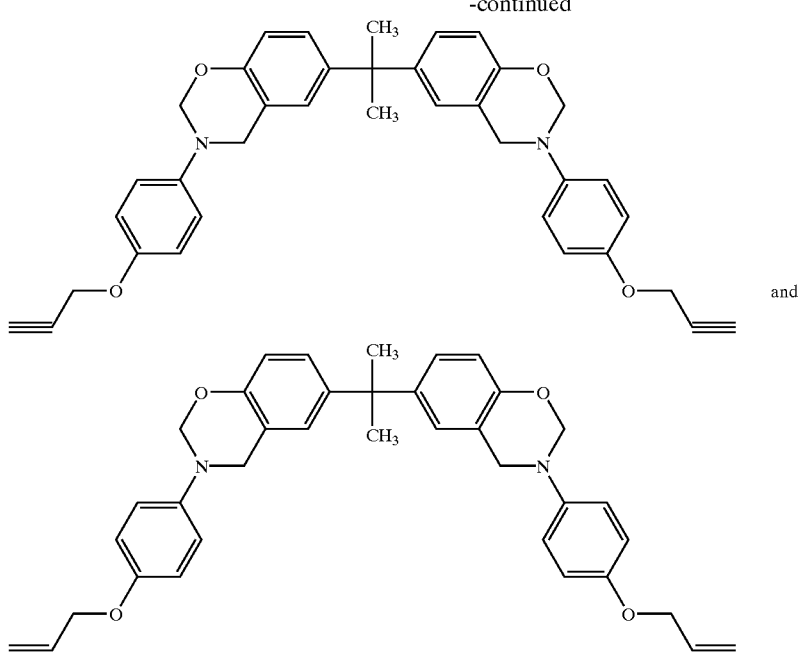

and

In addition to compounds such as the above, the benzoxazine may also be present in a polymeric species, such as the following:

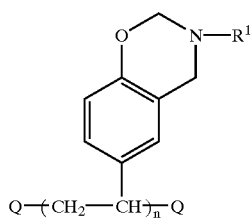

in which R¹ is as described above, n is an integer that will vary depending on the polymeric composition from which the benzoxazine depends, and each Q is a polymeric entity, for example, polyurethane, polyether, polyester, poly (butadiene) or polystyrenic.

The benzoxazine compound will be present in the curable composition in an amount within the range of 1% or more to 99% or less by weight of the combination of one or more benzoxazines and one or more other curable compounds or resins.

Preferred curable resins for blending with the benzoxazines include vinyl ethers, vinyl silanes, compounds or resins containing vinyl or allyl functionality, thiol-enes (a thiol-ene within this specification and claims is a compound or resin that is the reaction product of a thiol and a compound having carbon to carbon unsaturation), compounds or resins containing cinnamyl or styrenic functionality, fumarates, maleates, acrylates, maleimides, and cyanate esters.

Other curable resins for blending with the benzoxazines include hybrid resins that contain both epoxy and cinnamyl or styrenic functionality, hybrid resins that contain both vinyl silane and cinnamyl, styrenic, acrylate or maleimide functionality, hybrid resins that contain both vinyl silane and epoxy or vinyl ether functionality, and hybrid resins that contain both epoxy and acrylate or maleimide functionality.

Within the structures in this specification and claims, $C_{36}$ represents a mixture of isomers derived from linoleic and oleic acids having linear and branched alkyl chains with 36 carbon atoms.

Suitable curable compounds or resins having vinyl ether or allyl functionality for blending with benzoxazines include:

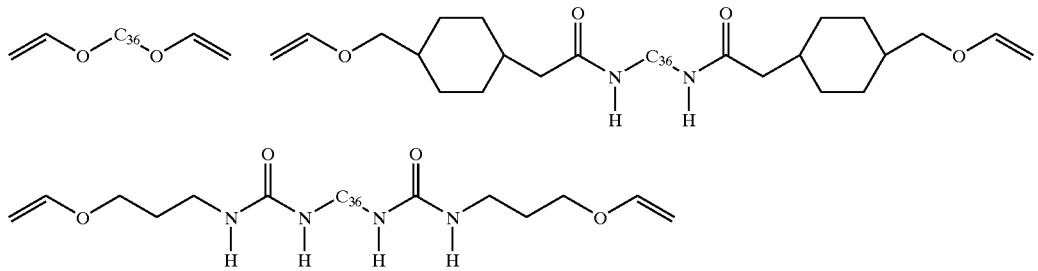

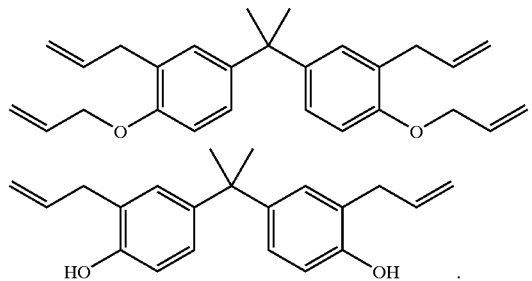

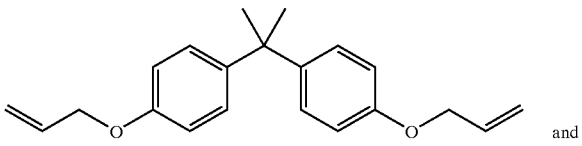
and

These compounds can be prepared by synthetic routes and from starting materials known to those skilled in the art. Other compounds containing vinyl ether or allyl functionality are commercially available from BASF, ISP, and Aldrich.

Suitable curable compounds or resins for blending with benzoxazines and containing both styrenic or cinnamyl and vinyl ether functionality are disclosed in U.S. Pat. No. 6,307,001 and include:

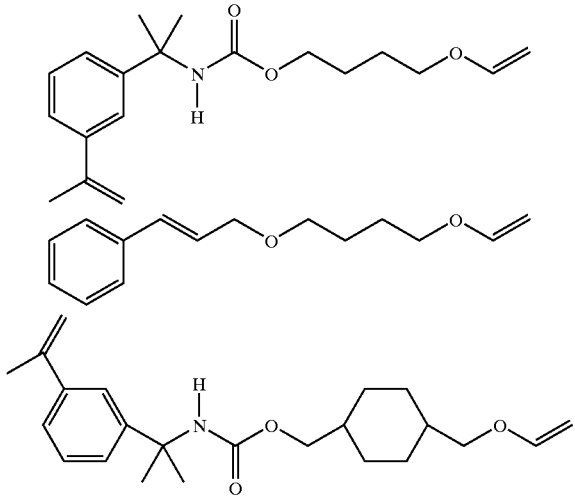

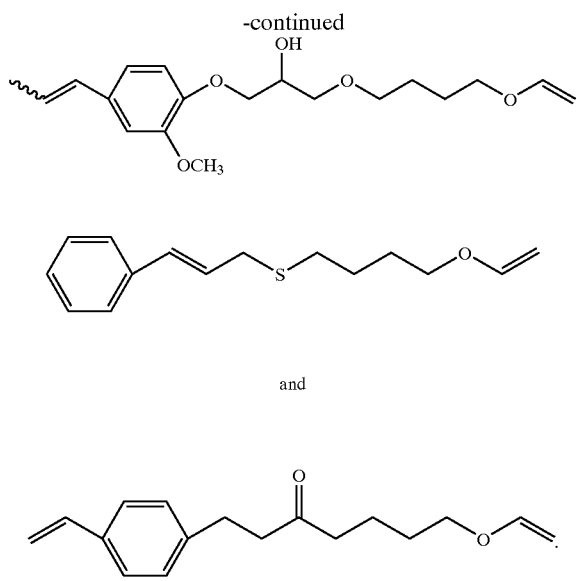
and

These compounds can be prepared by synthetic routes and from starting materials known to those skilled in the art, or by the routes disclosed in the identified patent.

Suitable curable compounds for blending with benzoxazine and containing styrenic or cinnamyl functionality include:

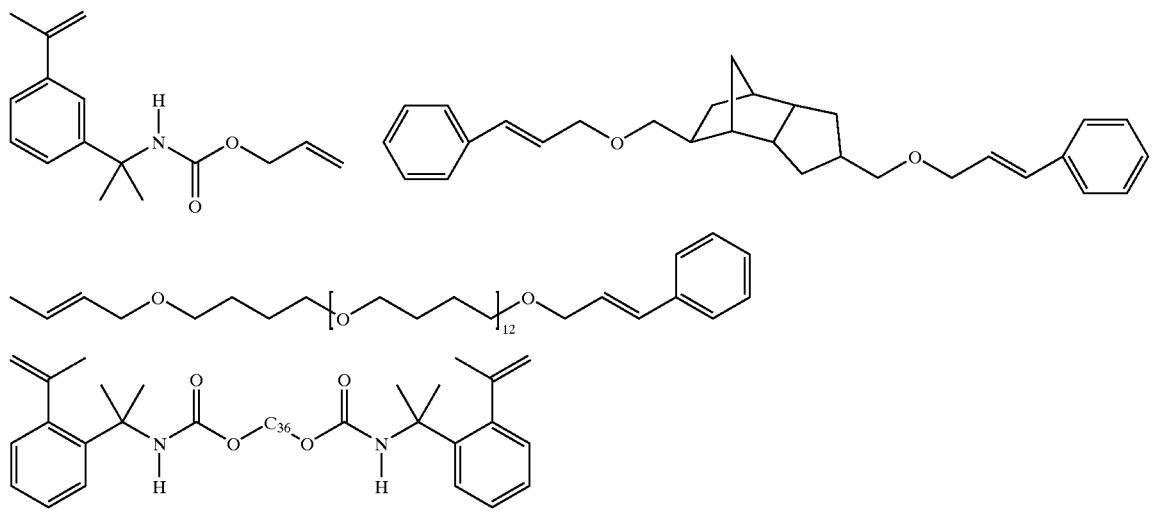

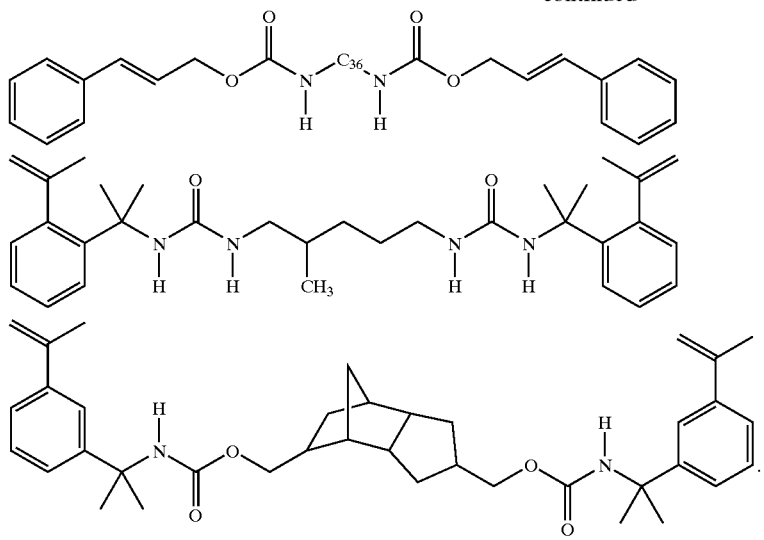

These compounds can be prepared by synthetic routes and from starting materials known to those skilled in the art.

Suitable curable compounds for blending with benzoxazine and containing alkoxy silane and styrenic, cinnamyl, vinyl ether or maleimide functionality include:

Suitable curable compounds or resins for blending with benzoxazine and containing styrenic or cinnamyl functionality with acrylate, maleate, fumarate or maleimide functionality, are disclosed in U.S. Pat. No. 6,300,456, and include:

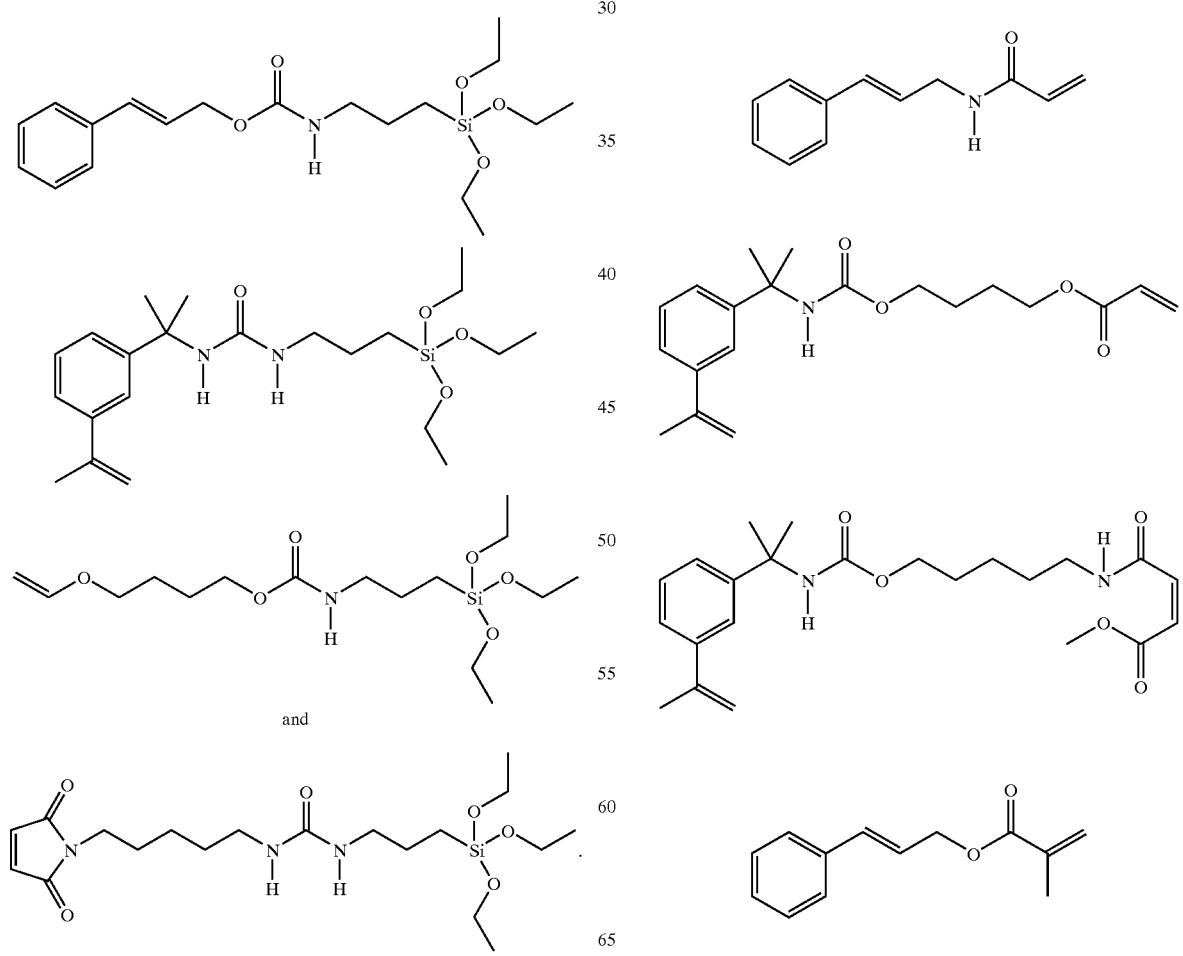

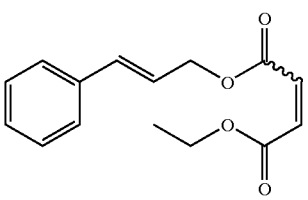
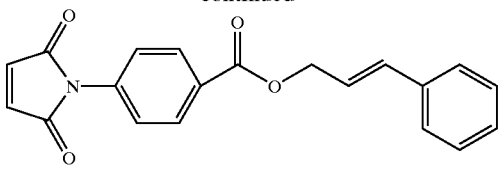
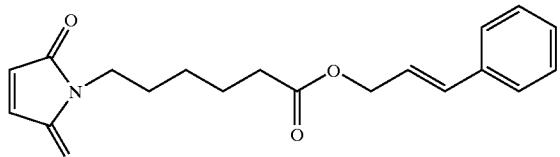
and
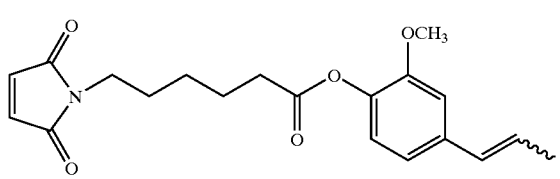
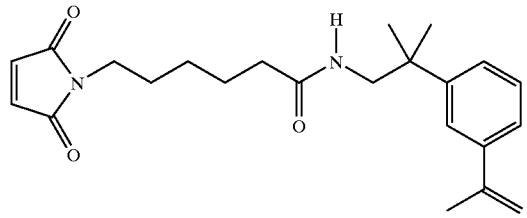
These compounds can be prepared by synthetic routes and from starting materials known to those skilled in the art, or by the routes disclosed in U.S. Pat. No. 6,300,456.
Additional curable maleimides for blending with benzoxazine are those disclosed in U.S. Pat. Nos. 6,057,381, 6,063,828, 6,180,187, 6,187,886, 6,281,314, and 6,265,530, and include:
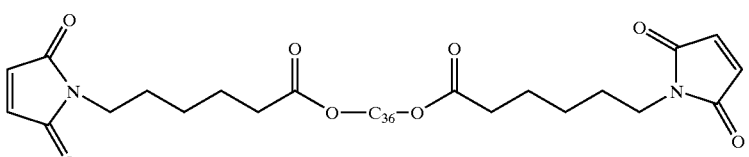
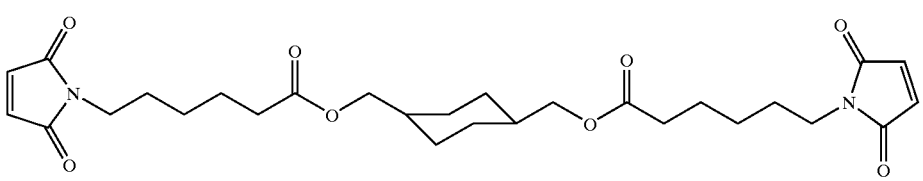
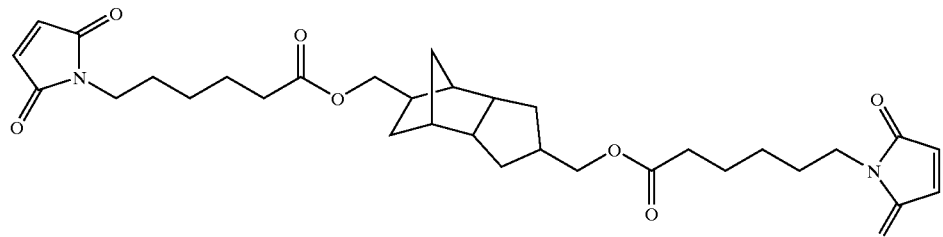
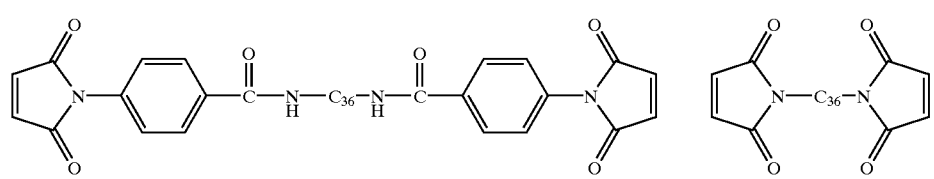

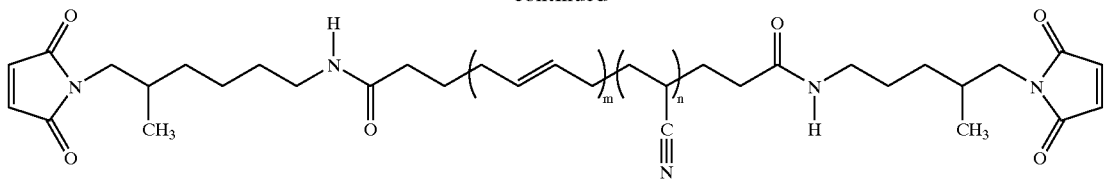

which resin is derived from a poly(butadiene) and in which m and n will vary depending on the particular poly(butadiene) starting material, (in one embodiment m and n will be integers to provide a number average molecular weight of 3600),

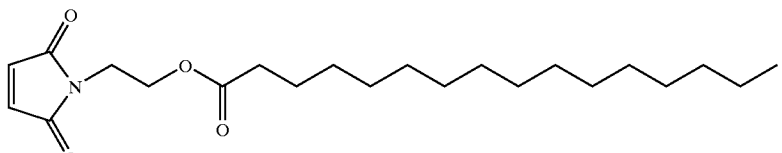

and

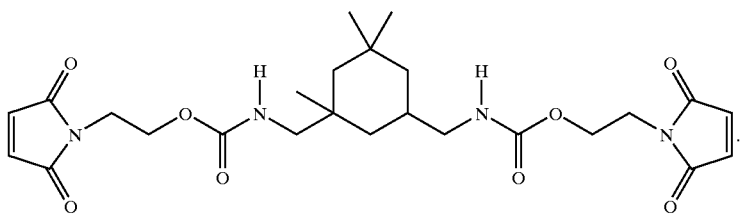

These compounds can be prepared by synthetic routes and from starting materials known to those skilled in the art, or by the routes disclosed in U.S. Pat. Nos. 6,057,381, 6,063,828, 6,180,187, 6,187,886, 6,281,314, and 6,265,530.

Additional curable maleates and fumarates for blending with benzoxazine are dioctyl maleate, dibutyl maleate, dioctyl fumarate, dibutyl fumarate. Additional maleate and fumarates are available from Aldrich.blended with benzox Additional curable resins containing both epoxy and electron acceptor or electron donor functionality may be azine. Electron donor functionality includes groups in which a carbon to carbon double bond is attached to an aromatic ring and conjugated with the unsaturation in the ring, such as styrenic or cinnamyl groups. Other electron donor groups include vinyl silanes and vinyl ethers. Electron acceptor functionality includes maleates, fumarates, acrylates and maleimides. Examples of compounds of this type include the following:

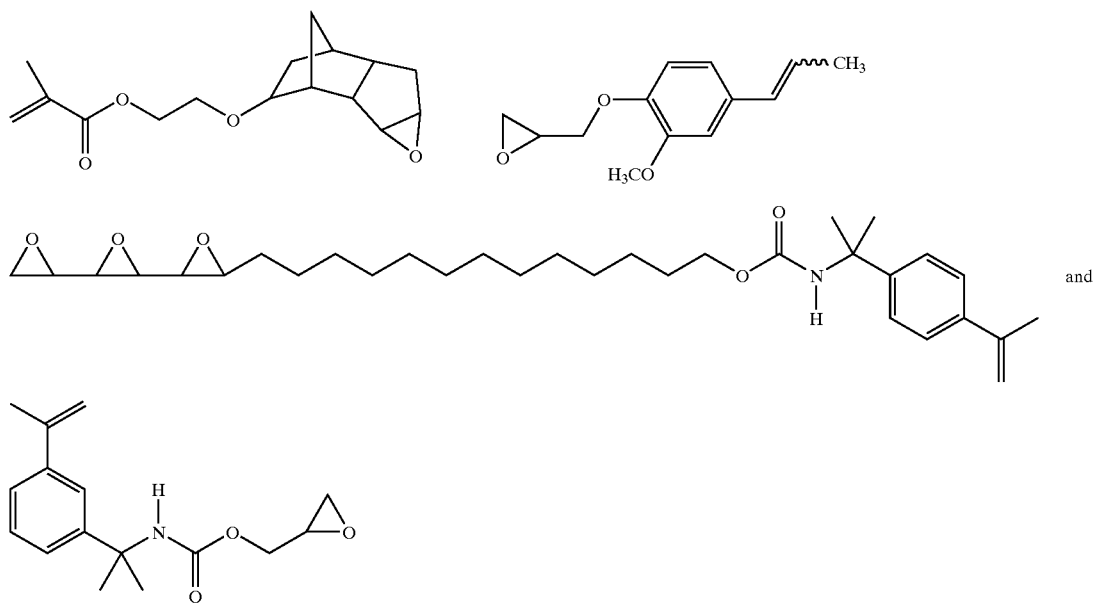

These compounds can be prepared by synthetic routes and from starting materials known to those skilled in the art.
Suitable curable compounds or resins containing both vinyl silane and electron donor or electron acceptor functionality for blending with benzoxazines include:
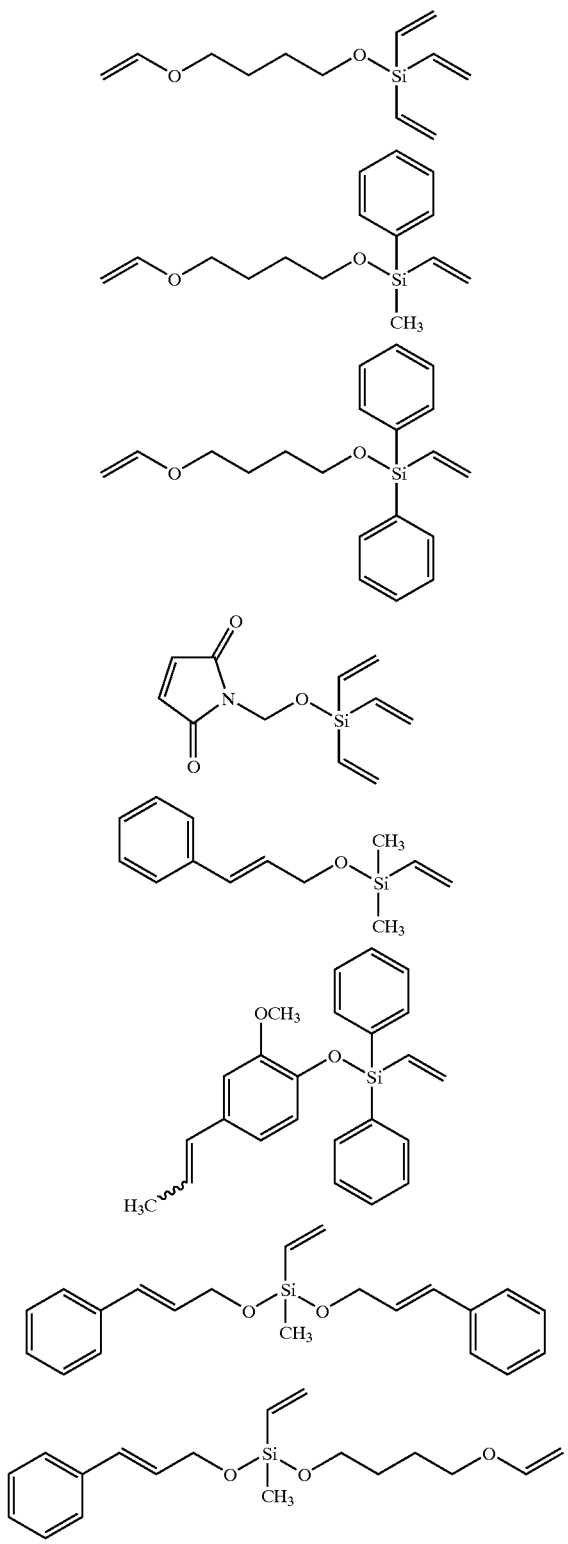
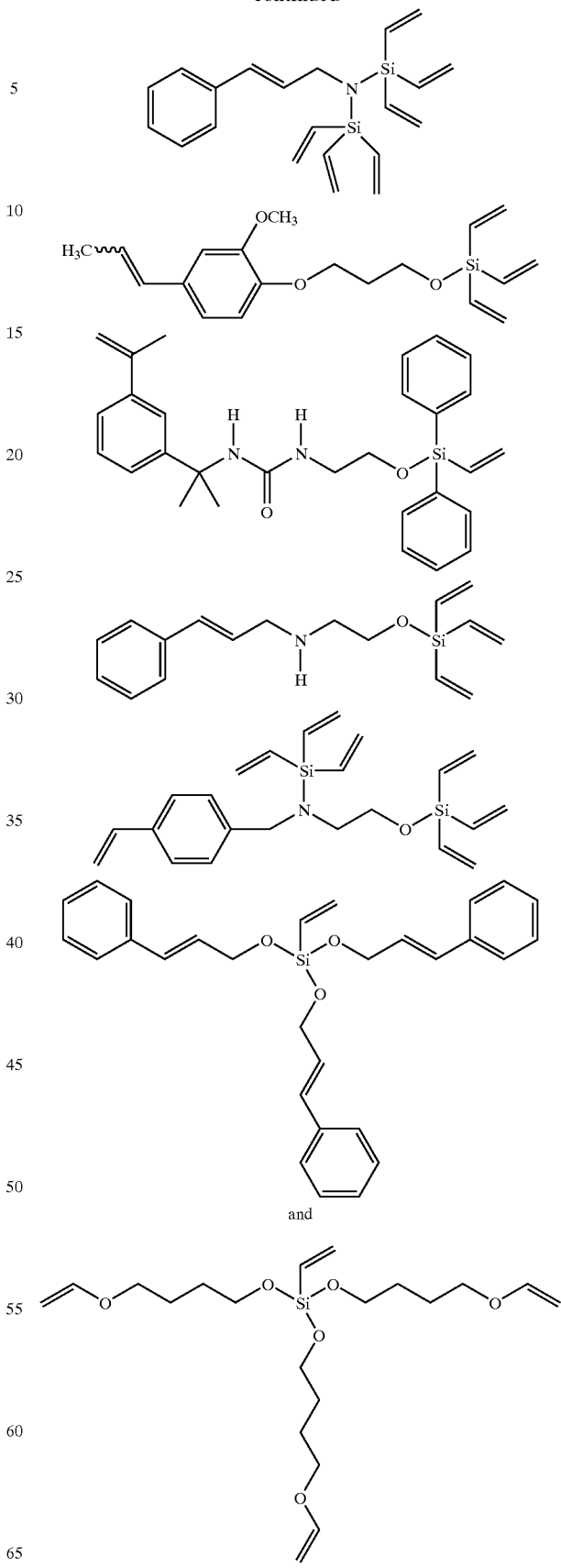
and These compounds can be prepared by synthetic routes and from starting materials known to those skilled in the art.

Suitable curable compounds or resins containing both vinyl silane and epoxy functionality for blending with benzoxazine include (in which t-Bu means a tertiary butyl group):

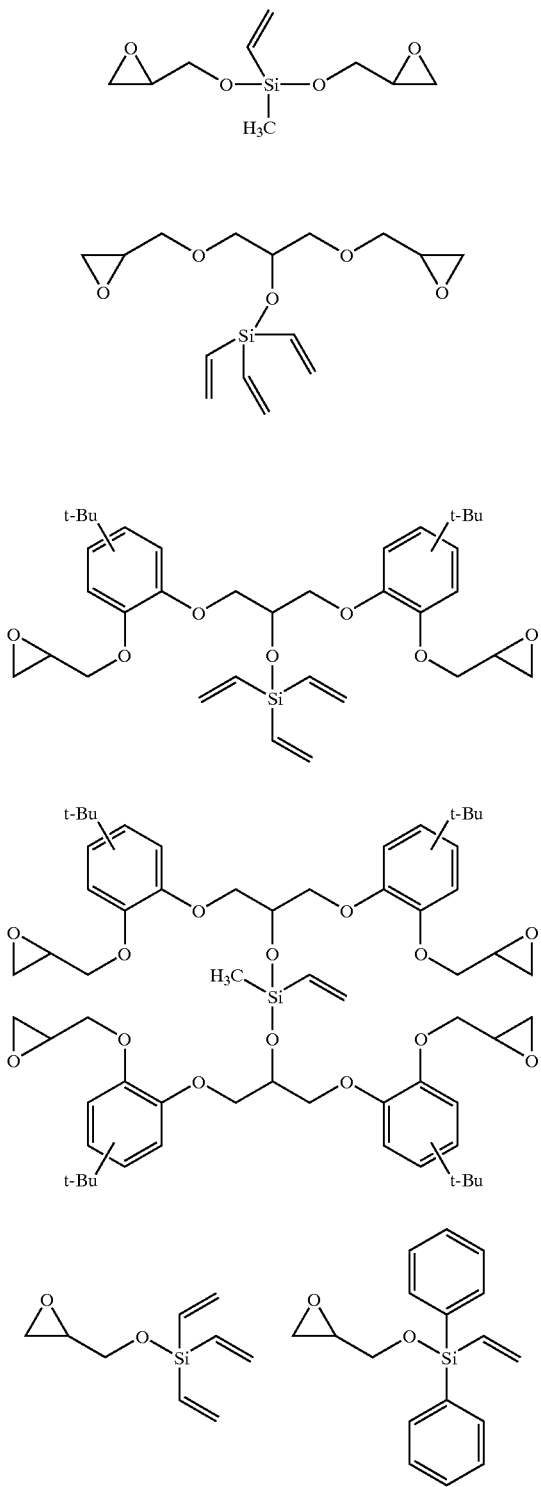

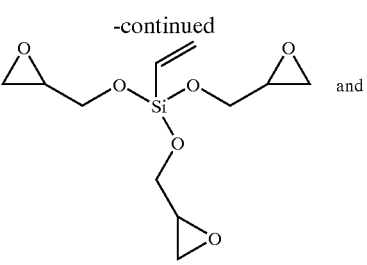

and

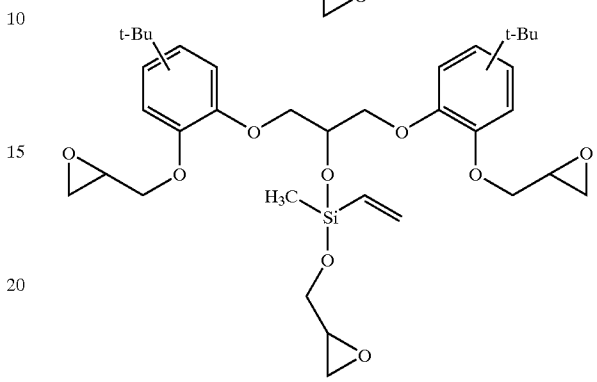

Suitable curable cyanate ester compounds or resins for blending with benzoxazine are those containing one or more cyanate ester functional groups, —OCN, and are commercially available from Ciby Geigy or Dow Chemical. Examples include 1,1'-bis(4-cyanatophenyl)ethane, bis(4-cyanate-3,5-dimethylphenyl)methane, 1,3-bis (cyanatophenyl-1-(1-methyl-ethylethyl-ethylidene)), 2,2'-bis(4-cyanatophenyl)isopropylidene Suitable thiol-enes for example, are those disclosed in U.S. Pat. Nos. 3,653,959, 4,422,914, 4,442,198, 4,443,495, 4,451,636, 4,481,281.

These compositions will cure with the application of heat, and in many cases will not need curing agents. If desired, curing agents can be added, such as, thermal initiators and photoinitiators present in an effective amount to cure the composition. In general, those amounts will range from 0.5% to 30%, preferably 1% to 20%, by weight of the total organic material (that is, excluding any inorganic fillers) in the composition. In general, the curable compositions will cure within a temperature range of 100° C. to 300° C., and curing will be effected within a range of ten seconds to three hours. The actual cure profile will vary with the components and can be determined without undue experimentation by the practitioner.

The curable compositions may also comprise nonconductive or thermally or electrically conductive fillers. Suitable nonconductive fillers are particles of vermiculite, mica, wollastonite, calcium carbonate, titania, sand, glass, fused silica, fumed silica, barium sulfate, and halogenated ethylene polymers, such as tetrafluoroethylene, trifluoroethylene, vinylidene fluoride, vinyl fluoride, vinylidene chloride, and vinyl chloride. Suitable conductive fillers are carbon black, graphite, gold, silver, copper, platinum, palladium, nickel, aluminum, silicon carbide, diamond, and alumina. If present, fillers generally will be in amounts of 20% to 90% by weight of the formulation.

The advantages of a composition comprising a blend of a benzoxazine-containing compound and another curable resin include the introduction of more flexibility and toughness to the benzoxazine as it co-reacts with the other resin, the ability to vary the cure temperature by varying the ratio of benzoxazine to the other curable resin, and the reduction of weight loss.

EXAMPLES

Example 1

The change in curing temperature of a blend of a benzoxazine compound and a second curable compound or resin is followed by Differential Scanning Calorimetry (DSC) as the weight ratio of benzoxazine to the second is varied. The results are reported in the following tables and show that the curing temperature of a blend of a benzoxazine and a second curable compound or resin can be varied by varying the ratio of the two components of the blend. The results from Examples 1A to 1G show that the curing temperature increases as the level of the curable compound or resin increases relative to the benzoxazine.

The curing profiles of these compounds indicate that they are suitable for use in the fabrication of semiconductors, particularly as die attach adhesives and films, and underfill materials, such as no-flow underfills, capillary flow underfills, wafer level underfills, and as lead free solders. For example, lead free tin solders melt at about 217° C., and the curing temperatures for underfill materials to support the solder after reflow should be above this temperature. As seen in the reported data, the blends of benzoxazine and other curable resins can be designed to cure in the range of 225° to 250° C.

In Examples 1A to 1F the benzoxazine is difunctional and has the structure:

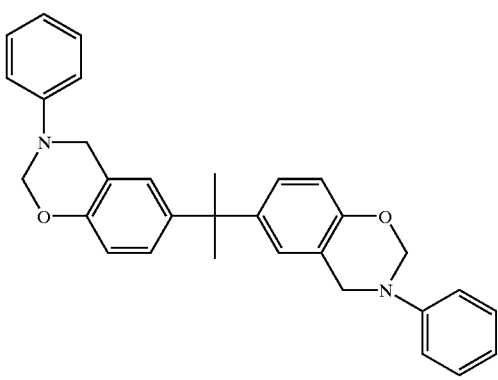

Example 1A

In this composition, the above benzoxazine was blended with a bismaleimide, designated BMI-1, having the following structure:

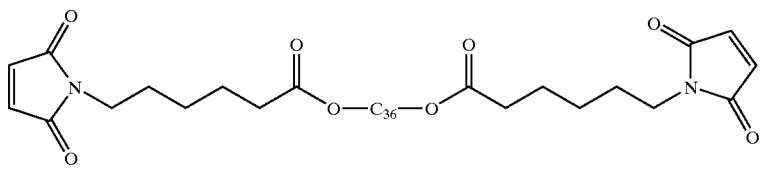

Variations in the curing temperature as the weight ratio of the components was varied are reported in Table 1A:

TABLE 1A

| DSC Curing Temperature for BMI-1/Benzoxazine | |
| --- | --- |
| BMI-1:Benzoxazine Weight ratio | DSC Curing Temperature (° C.) |
| 50:50 | 241.7 |
| 10:90 | 231.4 |
| 0:100 | 225.5 |

Example 1B

In this composition, the above benzoxazine was blended with a bismaleimide, designated BMI-2, having the following structure:

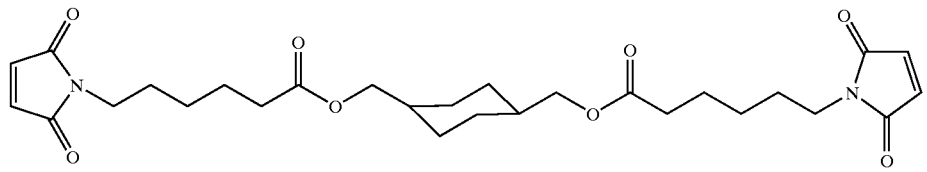

Variations in the curing temperature as the weight ratio of the components was varied are reported in Table 1B.

TABLE 1B

| DSC Curing Temperature for BMI-2/Benzoxazine | |
| --- | --- |
| BMI-2:Benzoxazine Weight ratio | DSC Curing Temperature (° C.) |
| 50:50 | 243.2 |
| 33:67 | 237.1 |
| 0:100 | 225.5 |

Example 1C

In this composition, the above benzoxazine was blended with a bismaleimide, designated BMI-3, having the following structure:

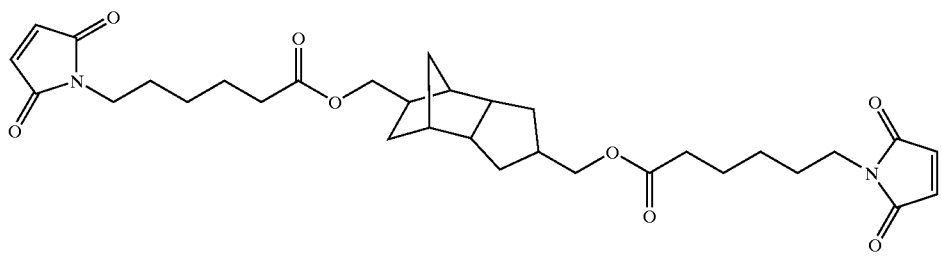

Variations in the curing temperature as the weight ratio of the components was varied are reported in Table 1C.

TABLE 1C

DSC Curing Temperature for BMI-3/Benzoxazine

| BMI-3:Benzoxazine Weight ratio | DSC Curing Temperature (° C.) |
|---|---|
| 100:0 | 225.5 |
| 50:50 | 228.3 |

Example 1D

In this composition, the above benzoxazine was blended with a styrenic compound, designated STY-1, having the following structure:

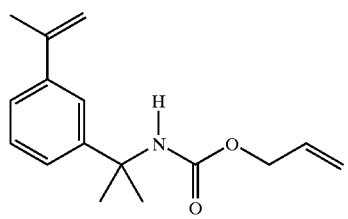

Variations in the curing temperature as the weight ratio of the components was varied are reported in Table 1D.

TABLE 1D

DSC Curing Temperature for STY-1/Benzoxazine

| STY-1:Benzoxazine Weight ratio | DSC Curing Temperature (° C.) |
|---|---|
| 50:50 | 247.3 |
| 10:90 | 228.5 |

TABLE 1D-continued

DSC Curing Temperature for STY-1/Benzoxazine

| STY-1:Benzoxazine Weight ratio | DSC Curing Temperature (° C.) |
|---|---|
| 2:98 | 226.8 |
| 0:100 | 225.5 |

Example 1E

In this composition, the above benzoxazine was blended with a cinnamyl compound, designated CIN-1, having the following structure:

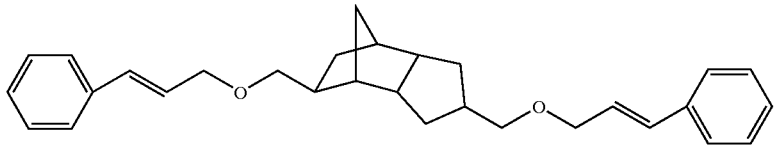

Variations in the curing temperature as the weight ratio of the components was varied are reported in Table 1E.

TABLE 1E

DSC Curing Temperature for CIN-1/Benzoxazine

| CIN-1:Benzoxazine Weight ratio | DSC Curing Temperature (° C.) |
|---|---|
| 50:50 | 238.0 |
| 10:90 | 228.3 |
| 2:98 | 225.7 |
| 0:100 | 225.5 |

Example 1F

In this composition, the above benzoxazine was blended with a hybrid acrylate/epoxy compound, designated ACR-1, having the following structure:

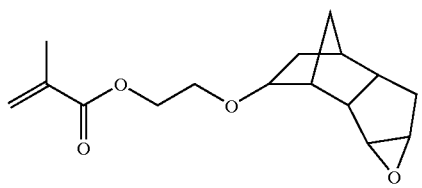

Variations in the curing temperature as the weight ratio of the components was varied are reported in Table 1F.

TABLE 1F

DSC Curing Temperature for ACR-1/Benzoxazine

| ACR-1:Benzoxazine Weight ratio | DSC Curing Temperature (° C.) |
|---|---|
| 50:50 | 241.6 |
| 10:90 | 229.8 |
| 2:98 | 229.3 |
| 0:100 | 225.5 |

Example 1G

In this composition, a mono-benzoxazine with the structure:

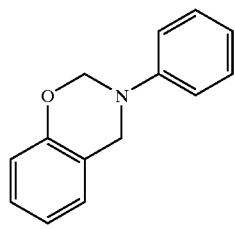

was blended with BMI-1 from Example 1A.

Variations in the curing temperature as the weight ratio of the components was varied are reported in Table 1G.

TABLE 1G

DSC Curing Temperature for BMI-1/Benzoxazine

| BMI-1:Benzoxazine Weight ratio | DSC Curing Temperature (° C.) |
|---|---|
| 50:50 | 251.6 |
| 10:90 | 243.0 |
| 2:98 | 240.2 |
| 0:100 | 239.4 |

Example 2

The Thermo Gravimetric Analysis (TGA) of the blend of the benzoxazine and BMI-1 from Example 1A was followed to determine if the benzoxazine and bismaleimide were co-reacting. The results are reported in Table 2 and show that the blend had a lower percent weight loss that either of the two components independently. This suggests that the benzoxazine and bismaleimide did react to form a higher molecular weight compound that was less volatile than the two co-reactants.

TABLE 2

TGA for BMI-2/Benzoxazine

| BMI-1:Benzoxazine Weight ratio | Percent Weight Loss (%) |
|---|---|
| 100:0 | 2.9 |
| 50:50 | 1.1 |
| 33:67 | 1.5 |
| 0:100 | 2.8 |

Example 3

Blends of the benzoxazine from Example 1A to 1F and other curable resins from Example 1 were heated to 225° C. for one hour, after which the glass transition temperature (Tg) was measured by Thermal Mechanical Analysis. The results are reported in Table 3 and show that the Tg varies as the ratio of the benzoxazine to other curable resin is varied.

TABLE 3

Variations in Tg with Variations in Weight Ratio of Benzoxazine and Other Curable Resins

| Weight ratio | Tg (° C.) |
|---|---|
| BMI-2:Benzoxazine | |
| 100:0 | −40 |
| 50:50 | 66 |
| 0:100 | 140 |
| BMI-3:Benzoxazine | |
| 100:0 | 50 |
| 50:50 | 107 |
| 0:100 | 140 |
| STY-1:Benzoxazine | |
| 50:50 | 121 |
| 0:100 | 140 |
| CIN-1:Benzoxazine | |
| 50:50 | 78 |
| 0:100 | 140 |
| ACR-1:Benzoxazine | |
| 50:50 | 96 |

Example 4

Curable die attach compositions were prepared and tested for adhesive strength. The control composition comprised a bismaleimide, a compound with cinnamyl functionality, curing agents, and 75% by weight silver. The inventive composition comprised the same formulation as the control with the addition of benzoxazine used in Example 1A to 1F in an amount of 20% by weight of the organic components.

Both compositions independently were dispensed onto a copper leadframe or onto a silver-coated copper leadframe. A silicon die (500×500 mil) was placed onto the composition on each leadframe and the resultant assembly placed in an oven at 175° C. for 30 minutes to cure the composition. Ten assemblies for each composition on each leadframe were prepared. Each die was sheared from its leadframe at 90 degrees with a Dage 2400-PC Die Shear Tester at 250°

C. The results were pooled and averaged and are reported in KgF in Table 4. The results show that the addition of the benzoxazine improves the adhesive strength of these compositions.

TABLE 4

Die Shear Strength AT 250° C. in KgF

| Formulation | On Cu leadframe | On Ag leadframe |
|---|---|---|
| Control | 11.5 | 23.8 |
| With Benzoxazine | 29.3 | 33.6 |

What is claimed:

1. A curable composition comprising a benzoxazine compound selected from the group consisting of:

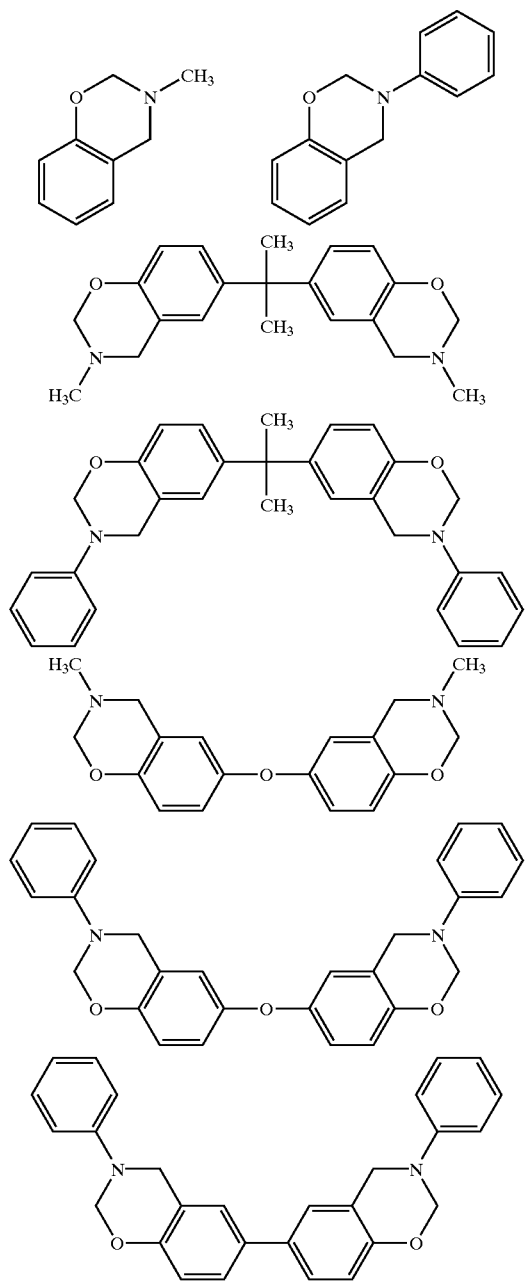
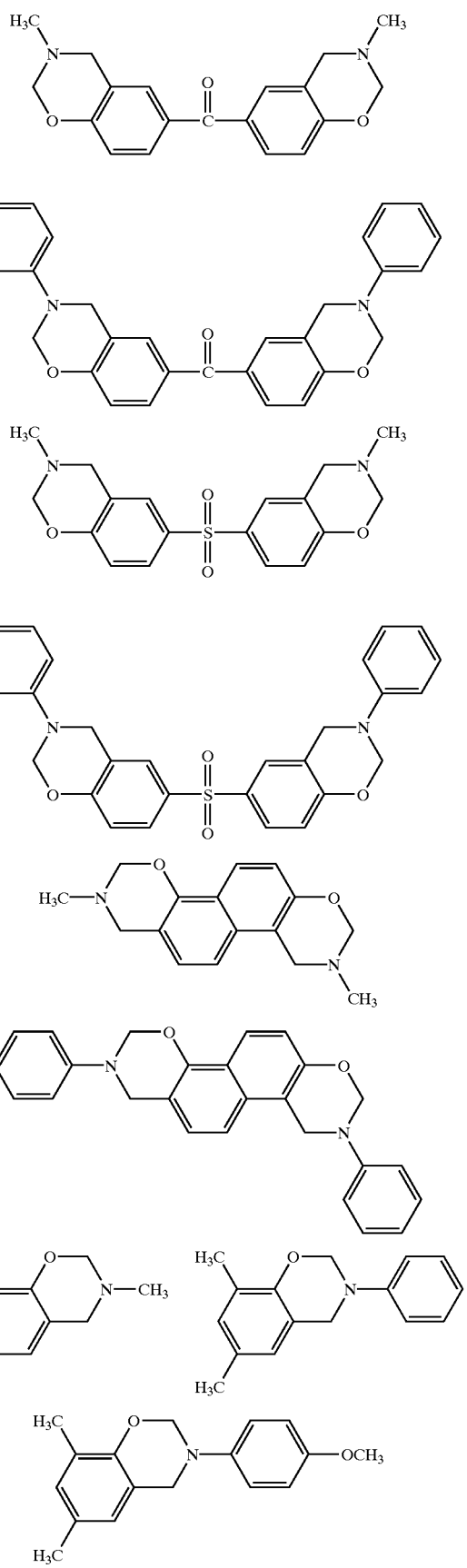

-continued
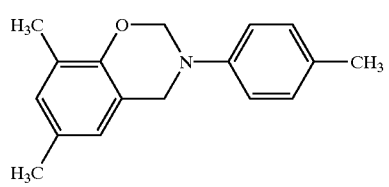
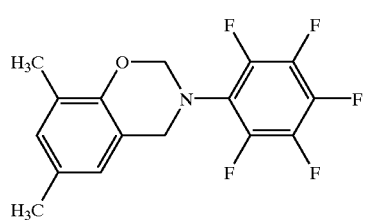
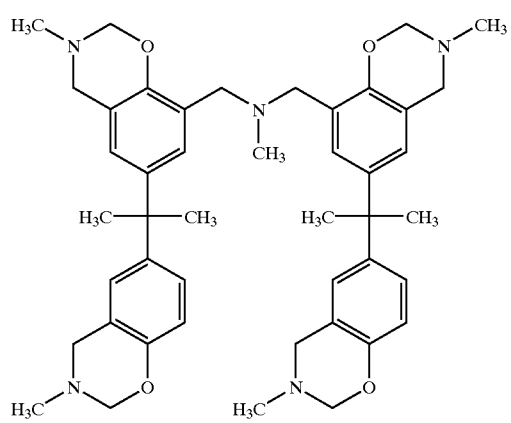
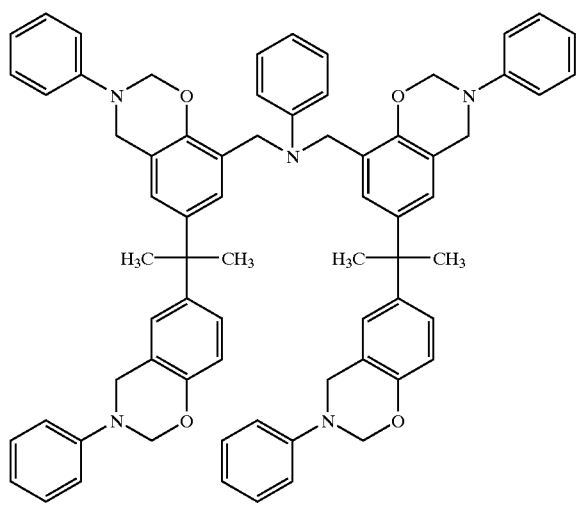
-continued
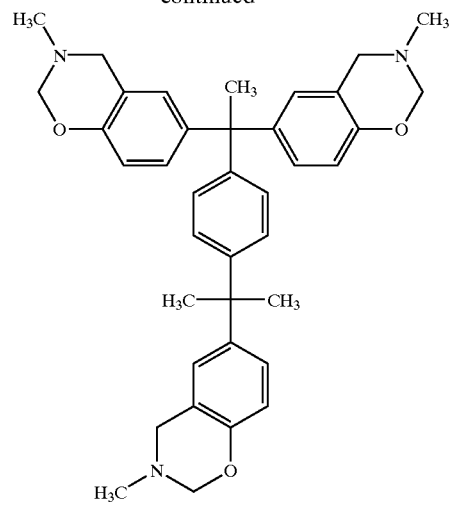
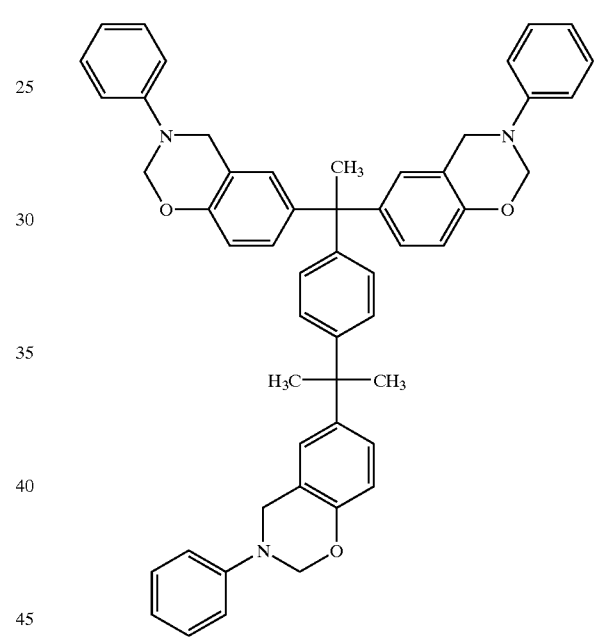
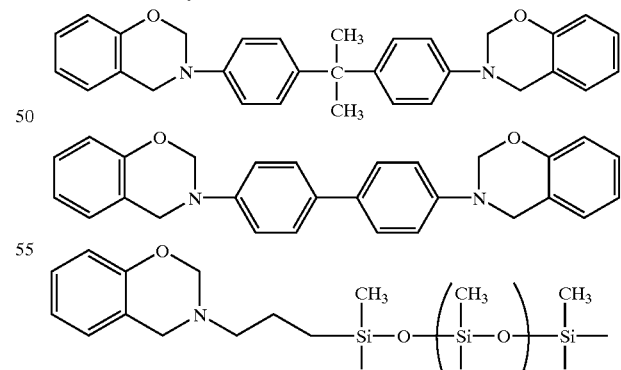
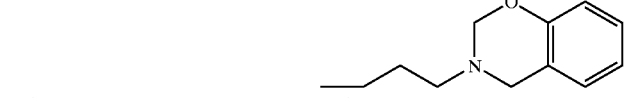
and -continued

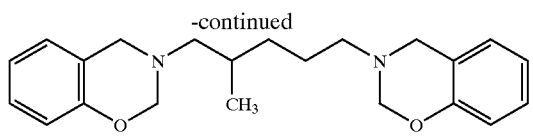

and a curable compound or resin selected from the group consisting of vinyl ethers, vinyl silanes, compounds or resins containing vinyl or allyl functionality, thiol-enes, compounds or resins containing cinnamyl or styrenic functionality, fumarates, maleates, acrylates, maleimides, cyanate esters, and hybrid resins containing contain both vinyl silane and cinnamyl, styrenic, acrylate or maleimide functionality.

2. The curable composition according to claim 1 in which the curable compound or resin is a vinyl ether.

3. The curable composition according to claim 1 in which the curable compound or resin is a vinyl silane.

4. The curable composition according to claim 1 in which the curable compound or resin is a compound or resin containing vinyl or allyl functionality.

5. The curable composition according to claim 1 in which the curable compound or resin is a thiol-ene.

6. The curable composition according to claim 1 in which the curable compound or resin is a compound or resin containing cinnamyl or styrenic functionality.

7. The curable composition according to claim 1 in which the curable compound or resin is a fumarate, maleate, or acrylate.

8. The curable composition according to claim 1 in which the curable compound or resin is a maleimide.

9. The curable composition according to claim 1 in which the curable compound or resin is a cyanate ester.

10. The curable composition according to claim 1 in which the curable compound or resin is a hybrid resin containing both vinyl silane and cinnamyl, styrenic, acrylate or maleimide functionality.

* * * * *